US008012484B2

(12) United States Patent
Linden et al.

(10) Patent No.: US 8,012,484 B2
(45) Date of Patent: Sep. 6, 2011

(54) METHOD OF TREATING ISCHEMIA REPERFUSION INJURY BY INHIBITING NKT CELL ACTIVITY

(75) Inventors: Joel M. Linden, La Jolla, CA (US); Courtney M. Lappas, Mclean, VA (US); Victor H. Engelhard, Crozet, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 41 days.

(21) Appl. No.: 12/054,643

(22) Filed: Mar. 25, 2008

(65) Prior Publication Data

US 2008/0254037 A1    Oct. 16, 2008

Related U.S. Application Data

(60) Provisional application No. 60/923,081, filed on Apr. 12, 2007.

(51) Int. Cl.
*A61K 39/395* (2006.01)
*C07K 16/00* (2006.01)
*C12P 21/08* (2006.01)

(52) U.S. Cl. ............... 424/152.1; 424/130.1; 530/387.1; 530/388.73; 530/388.75

(58) Field of Classification Search ........................ None
See application file for complete search history.

(56) References Cited

U.S. PATENT DOCUMENTS

2002/0165170 A1   11/2002   Wilson et al.
2004/0087485 A1   5/2004    Iian et al.

OTHER PUBLICATIONS

Day Y-J et al. Am. J. Physiol. Gastrointest. Liver Physiol. 286:G285-G293, 2004.*
Day Y-J et al. J. Immunol. 174:5040-5046, 2005.*
Lappas CM et al. J. Immunol. 174:1073-1080, 2005.*
Kronenberg M et al. Annu. Rev. Immunol. 23:877-900, 2005.*
Lappas CM et al. J. Exp. Med. 203(12):2639-2648, Nov. 27, 2006.*
Amiot, M. , et al., "Heterogeneity of the First Cluster of Differentiation: Characterization and Epitopic Mapping of Three CD1 Molecules on Normal Human Thymus Cells", *The Journal of Immunology*, 136(5), (1986),1752-1758.
Koch, M. , et al., "The Crystal Structure of Human CD1 With and Without alpha-Galactosylceramide", *Nature Immunology*, 6(8), (2005),819-826.
Ulrichs, T. , et al., "T-Celll Responses to CD1-Presented Lipid Antigens in Humans with Mycobacterium tuberculosis Infection", *Infection and Immunity*, 71(6), (2003),3076-3087.
Bendelac, A., et al., "Mouse CD1-Specific NK1 T Cells: Development, Specificity, and Function", *Annu. Rev. Immunol.*, 15, (1997), 535-562.
Chen, J.-F., et al., "A2A Adenosine Receptor Deficiency Attenuates Brain Injury Induced by Transient Focal Ischemia in Mice", *The Journal of Neuroscience*, 19(21), (1999), 9192-9200.

Cronstein, B. N., "Adenosine, an Endogenous Anti-Inflammatory Agent", *Journal of Applied Physiology*, 76(1), (1994), 5-13.
Day, Y. J, et al., "Renal ischemia-reperfusion injury and adenosine 2A receptor-mediated tissue protection: the role of $CD4^+T$ cells and $IFN-\gamma$.", *J Immunol.*, 176(5), (2006), 3108-3114.
Godfrey, D. I., et al., "NKT cells: facts, functions and fallacies", *Immunology Today*, 21, (2000), 573-583.
Godfrey, D. I., et al., "NKT cells: what's in a name?", *Nature Reviews Immunology*, 4, (2004), 231-237.
Hammond, K. J. L., et al., "CD1d-Restricted NKT Cells: An Interstrain Comparison", *The Journal of Immunology*, 167, (2001), 1164-1173.
Hansen, D. S., et al., "Regulation of immunity and pathogenesis in infectious diseases by CD1d-restricted NKT cells", *International Journal for Parasitology*, 34, (2004), 15-25.
Kawano, T., et al., "Natural killer-like nonspecific tumor cell lysis mediated by specific ligand-activated $V\alpha14$ NKT cells", *Proc. Natl. Acad. Sci. USA*, 95, (1998), 5690-5693.
Kurokawa, T., "Beneficial Effects of Cyclosporine on Postischemic Liver Injury in Rats", *Transplantation*, 53(2), (1992), 308-311.
Linden, J., "Adenosine in Tissue Protection and Tissue Regeneration", *Molecular Pharmacology*, 67(5), (2005), 1385-1387.
Linden, J., "Molecular Approach to Adenosine Receptors: Receptor-Mediated Mechanisms of Tissue Protection", *Annual Review of Pharmacology and Toxicology*, 41, (2001), 775-787.
Mercer, J. C., et al., "Natural killer T cells: rapid responders controlling immunity and disease", *The International Journal of Biochemistry & Cell Biology*, 37, (2005), 1337-1343.
Ohta, A., "Role of G-protein-coupled adenosine receptors in downregulation of inflammation and protection from tissue damage", *Nature*, 414(6866), (2001), 916-920.
Sakr, M. F., et al., "Protective Effect of Cyclosporine A (CyA) Against the Hepatic Injury Associated with Ischemia and Reperfusion", *Int. Surg.*, 81, (1996), 180-183.
Savransky, V., et al., "Role of the T-cell receptor in kidney ischemia-reperfusion injury", *Kidney International*, 69(2), (2006), 233-238.
Shimamura, K., et al., "Association of NKT cells and granulocytes with liver injury after reperfusion of the portal vein", *Cell Immunology*, 234(1), (Abstract Only), (2005), 31-38.
Sullivan, G. W., et al., "Adenosine and Related Compounds Counteract Tumor Necrosis Factor-$\alpha$ Inhibition of Neutrophil Migration: Implication of a Novel Cyclic AMP-Independent Action on the Cell Surface", *The Journal of Immunology*, 145(5), (1990), 1537-1544.
Sullivan, G. W., et al., "Cyclic AMP-Dependent Inhibition of Human Neutrophil Oxidative Activity by Substitued 2-Propynylcyclohexyl Adenosine $A_{2A}$ Receptor Agonists", *British Journal of Pharmacology*, 132(5), (2001), 1017-1026.
Watanabe, Y., et al., "Interferon-$\gamma$ Induces Reactive Oxygen Species and Endoplasmic Reticulum Stress at the Hepatic Apoptosis", *Journal of Cellular Biochemistry*, 89, (2003), 244-253.
Yang, Z., "Infarct-Sparing Effect of $A_{2A}$-Adenosine Receptor Activation Is Due Primarily to Its Action on Lymphocytes", *Circulation*, 111(17), (2005), 2190-2197.
Yokota, N., et al., "Protective Effect of T Cell Depletion in Murine Renal Ischemia-Reperfusion Injury", *Transplation*, 74(6), (2002), 759-763.

(Continued)

*Primary Examiner* — Robert Landsman
(74) *Attorney, Agent, or Firm* — Schwegman, Lundberg & Woessner, P.A.

(57) ABSTRACT

The present invention relates to a method for treating recurrent tumor metastases following liver resection that includes administration of an effective amount of an agonist of $A_{2A}$ adenosine receptors (ARs).

10 Claims, 11 Drawing Sheets

OTHER PUBLICATIONS

Yu, K. O., et al., "The diverse functions of CD1d-restricted NKT cells and their potential for immunotherapy", *Immunology Letters*, 100, (2005), 42-55.

Zhou, D., et al., "Lysosomal Glycosphingolipid Recognition by NKT Cells", *Science*, 306(5702), (2004), 1786-1789.

* cited by examiner

SHAM　　　　　　VEHICLE　　　　　　PKL136

ISCHEMIA REPERFUSION INJURY
↓
LIPID PRESENTATION BY CD1d TO Vα 14Jα18 TCR
↓
CD4+NK1.1+ iNKT CELL
↓ ⊣ $A_{2A}$ R AGONIST
IFN-γ
↓
PMN
↓
TISSUE NECROSIS

*Fig. 6*

METHOD OF TREATING ISCHEMIA REPERFUSION INJURY BY INHIBITING NKT CELL ACTIVITY

RELATED APPLICATIONS/PATENTS

This application claims priority under 35 U.S.C. §119(e) from U.S. Provisional Application Ser. No. 60/923,081 filed Apr. 12, 2007, which is herein incorporated by referenced.

US GOVERNMENT RIGHTS

This invention was made with the United States Government support under Grant No. R01 HL37942 awarded by the National Institutes of Health. The United States Government has certain rights in the invention.

FIELD OF THE INVENTION

The present invention relates to method for treating ischemia reperfusion injury that includes administration of an effective amount of an agent that inhibits NKT cell activity.

BACKGROUND OF THE INVENTION

Reperfusion injury following hepatic ischemia is associated with inflammation and ongoing necrosis that is amplified by deletion of the $A_{2A}$ adenosine receptor ($A_{2A}R$)[1]. The activity of most inflammatory cells, including but not limited to macrophages, monocytes, T lymphocytes, platelets and polymorphonuclear leukocytes, is inhibited by the activation of the anti-inflammatory Gs-coupled $A_{2A}R$, resulting in reduced pro-inflammatory cytokine production and diminished endothelial adhesion molecule expression[2-7]. Accumulating evidence suggests that hepatic reperfusion injury is triggered by lymphocyte activation[1] and that the activation of $A_{2A}Rs$ on bone-marrow-derived cell mediates liver protection[8]. These findings, and studies establishing that the activation of the $A_{2A}R$ on CD4+ T cells inhibits TCR-mediated IFN-γ production in vitro[3], suggest that treatment with the selective $A_{2A}R$ agonist, 4-{3-[6-Amino-9-(5-ethylcarbamoyl-3,4-dihydroxy-tetrahydro-furan-2-yl)-9H-purin-2-yl]-prop-2-ynyl}-cyclohexanecarboxylic acid methyl ester (ATL146e), may mediate protection from hepatic ischemia reperfusion injury (IRI) by inhibiting the activation of CD4+ T lymphocytes. However, the rapidity of reperfusion injury is not consistent with the timeframe required for activation and differentiation of conventional CD4+ T cell responses, suggesting it is mediated by a rapidly activated T cell subset.

Most therapeutic studies involving CD1-restricted T cells have been confined to the use of a population of CD1d-restricted T cells, which expresses natural killer (NK) cell markers such as NK 1.1 and a T cell receptor (TCR) consisting of an invariant α-chain (Vα14Jα18 in mice and Vα24Jα18 in humans), which pairs with one of a limited number of β-chains. In both species, these "invariant" NKT cells display rapid and potent cytolytic activity and secretion of cytokines (IFN-γ, IL-2, IL-4 and IL-10), which direct adaptive immune responses.

The majority of mouse CD4+NK1.1+ natural killer T cells express the invariant TCR, Vα14Jα18, and are dependent on CD1d for positive selection in the thymus and subsequent activation in the periphery[9;10]. CD1d is expressed by hepatocytes, gut epithelial cells and APCs and presents either self glycolipid, such as isoglobotrihexosylceramide[11], or foreign glycolipid, such as the marine sponge-derived α-Gal-Cer[12], to NKT cells. The rapid release of IFN-γ or IL-4 following activation of invariant NKT (iNKT) cells by CD1d-glycolipid presentation to TCRs has been attributed to pre-formed cytokine transcripts[13]. Although NKT cells comprise only 0.1-3% of the T lymphocyte population in blood and spleen, in the murine liver NKT cells account for as much as 30% of the total lymphocyte population and as much as 50% of total αβ TCR+ T cells[14]. The high abundance of NKT cells in the liver and their rapid response to activation suggests that they might play a role in hepatic reperfusion injury. We show that NKT cells are involved in the pathogenesis of hepatic IRI and that they comprise a subset of CD4+ T lymphocytes through which ATL146e mediates liver protection.

While mice encode a single CD1 isoform, CD1d, humans have five isoforms, CD1a-e, of which CD1a, CD1b, CD1c and CD1d have been shown to stimulate T cells. CD1a, b and c are expressed by dendritic cells and other antigen-presenting cells and can present a range of lipids (mycolic acids, mycolates esterified to simple sugars, phosphatidyl inositol moieties linked to complex glycans, polyisoprenoid lipids and lipopeptides) derived from the cell walls of mycobacteria to T cells. CD1d is expressed by various myeloid, epithelial, parenchymal, and vascular smooth muscle cells in non-lymphoid organs and can present the α-anomeric glycolipid, α-galactosylceramide (αGC), found in marine sponges and glycosphingolipids from Gram-negative bacteria that do not contain lipopolysaccharide to subsets of T cells. Many CD1-restricted T cells can also be stimulated by exposure to antigen-presenting cells expressing CD1a, CD1b, CD1c or CD1d in the absence of added antigen. This autoreactivity probably results from T cell recognition of endogenous lipid antigens, such as phospholipids, gangliosides, sulphatides and the lysosomal glycosphingolipid, isoglobotrihexosylceramide, which have been shown to bind to human and murine CD1 and activate CD1-restricted T cells.

SUMMARY OF THE INVENTION

The present invention provides a novel method for treating ischemia reperfusion injury comprising administering to a patient in need thereof a therapeutically effective amount of an agent that inhibits NKT cells.

The present invention also provides pharmaceutical compositions comprising an agent that inhibits NKT cells and a pharmaceutically acceptable excipient.

The present invention provides an agent for use in medical therapy.

The present invention also provides the use of an agent that inhibits NKT cells for the manufacture of a medicament for the treatment of ischemia reperfusion injury.

These and other objects, which will become apparent during the following detailed description, have been achieved by the inventors' discovery that an agent that inhibits NKT can be used to treat hepatic ischemia reperfusion injury.

BRIEF DESCRIPTION OF THE DRAWINGS

The accompanying drawings, which are incorporated herein and form a part of the specification, illustrate some aspects of the present invention and together with the description, serve to explain the principles of the invention.

FIG. 6. Hypothetical scheme of reperfusion-induced inflammatory injury in the liver. Reperfusion results in the generation of reactive oxygen species and $H_2O_2$, and also in the CD1d-dependent activation of NKT cells. NKT cells are activated to produce IFN-γ early after the initiation of reperfusion, and this activation is inhibited by $A_{2A}R$ activation. As a consequence of this inhibition, downstream events in the reperfusion-induced inflammatory cascade (including neutrophil accumulation and tissue necrosis) are significantly reduced by ATL146e treatment.

DETAILED DESCRIPTION OF THE INVENTION

Figure 1:
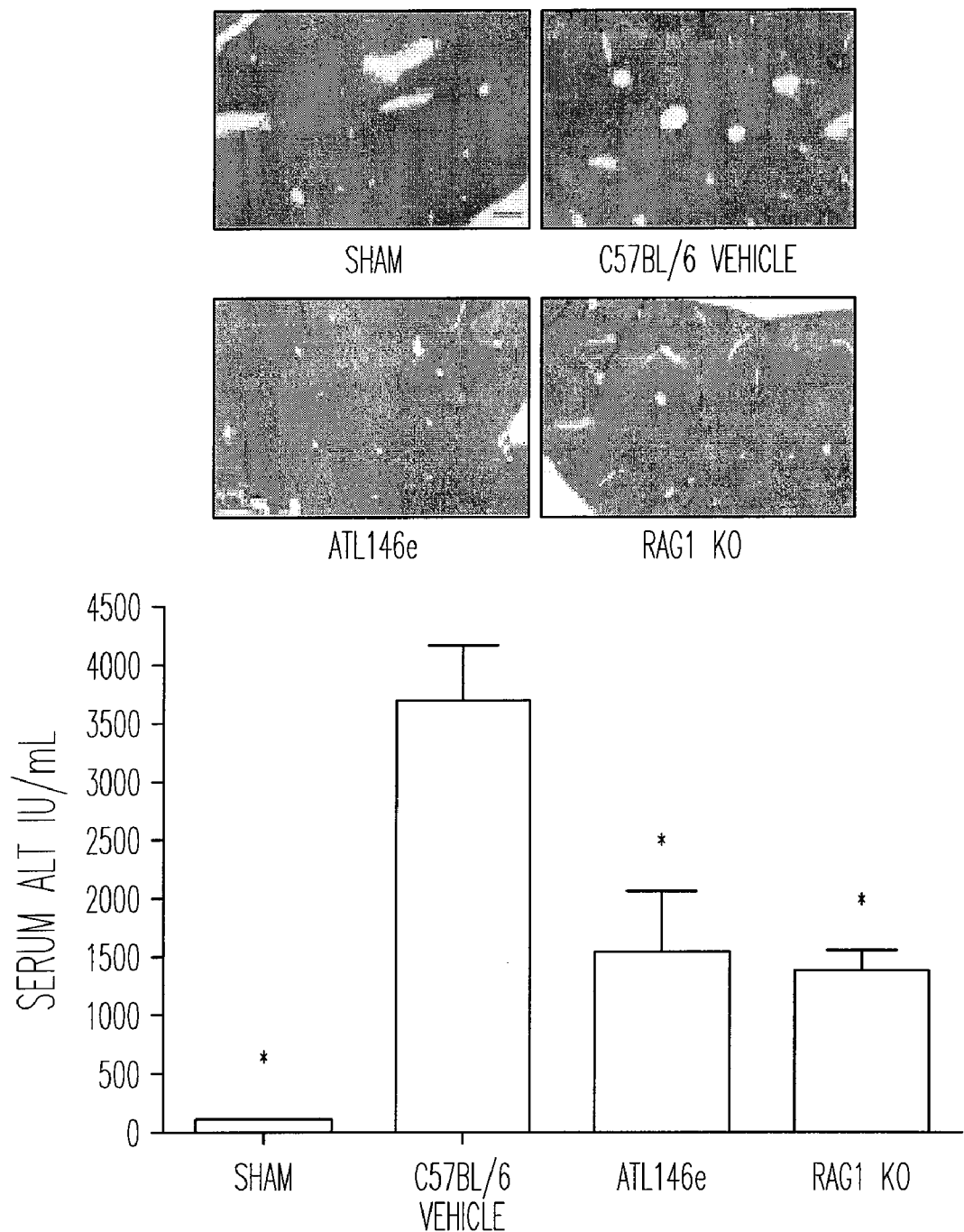
FIG. 1. Protection from hepatic IRI by $A_{2A}R$ activation or lymphocyte deficiency. WT or Rag 1 KO C57BL/6 mice were subjected to 72 minutes of hepatic ischemia followed by 24 hours of reperfusion, or sham surgeries. Immediately after the initiation of reperfusion animals received ATL146e or vehicle control (A). Animals were sacrificed by cervical dislocation after 24 hours of reperfusion, blood was collected via retro-orbital bleed and serum ALT was measured. Additionally, livers were perfused and left liver lobes were collected and placed immediately into 4% paraformaldehyde. Necrosis was measured via H and E staining. Data shown are from three independent experiments (N=9); error bars indicate SEM. *p<0.01 vs. C57BL/6 vehicle control as assessed by one way ANOVA followed by Dunnetts multiple comparison test. H and E staining shown is representative of 5 10× fields of view photographed for each of nine animals in three independent experiments.

In light of this discovery, the present invention provides a novel method for treating ischemia reperfusion injury (IRI), comprising: administering to a patient in need thereof a therapeutically effective amount of an agent that inhibits NKT cells. The agent can inhibit NKT cells by a number of mechanisms including depleting/reducing the number NKT cells present (e.g., using an anti-NKT antibody) and preventing their activation (e.g., using an anti-CD1 antibody). The agent can be an antibody, small molecule, or any other pharmaceutically acceptable active that would be useful in inhibiting NKT cells. Examples of the injury include heart, kidney, skin, and liver ischemia-reperfusion injury. As used herein, treating IRI also includes treating the effects of tissue transplantation and sickle cell disease, which have been found to be ischemic in nature (e.g., see U.S. Ser. No. 11/673,360).

An example of an anti-NK1.1 antibody is PK136. Examples of anti-CD1 antibodies include an anti-CD1a, anti-CD1b, anti-CD1c, or anti-CD1d antibody. Specific examples of anti-CD1 antibodies include 10H3.9.3 (CD1a), BCD1b3 (CD1b), F10/21A3 (CD1c) and CD1d51 (CD1d). Antibodies from additional clones could also be used, including, but not limited to, B330, NA1/34, NA1/34-HLK, RIV12, HI149, CD1a007, O10, SPM120, NOR3.2, B-B5, CBT6, M1-2-1B5, B17.20.9, BL6, MTB1, 66IIC7, 100-1A5, M1-2-1B5, M-T101, 4A7.6, WM25, SN13/K5-1B8, L161, M241, 4B11, 11.86, AD5-8E7, CD1d42, and C3D5.

The timing of the present method of treating will depend upon the selected agent. If a depleting agent is used (e.g., an antibody that depletes NKT cells), then the therapy will need to be started early enough to allow for depletion of NKT cells (e.g., 1, 2, 3 or more days before a scheduled surgery). If the agent selected has a more rapid activity (e.g., an antibody that blocks the activation of NKT cells), then the therapy can be started much closer to a surgery (e.g., 0.5 or 1 day beforehand). Agents with even more rapid activity (e.g., a small molecule with rapid onset of activity) could be administered hours before surgery. Therapy with agents that block or inhibit the activation of NKT cells can be continued post surgery (e.g., for an additional 0.5, 1, 2, or more days) in order to continue to benefit from the inactivation of NKT cells.

Ischemia reperfusion injury results from tissue damage during ischemia and ongoing inflammation and injury during reperfusion. Liver reperfusion injury is reduced by lymphocyte depletion or activation of adenosine $A_{2A}$ receptors with the selective agonist 4-{3-[6-amino-9-(5-ethylcarbamoyl-3,4-dihydroxy-tetrahydro-furan-2-yl)-9H-purin-2-yl]-prop-2-ynyl}-cyclohexanecarboxylic acid methyl ester (ATL146e).

It is shown herein that NKT cells are stimulated to produce IFN-γ by 2 hours after the initiation of reperfusion, and the use of antibodies to deplete NK1.1 positive cells (NK and NKT) or to block CD1d-mediated glycolipid presentation to NKT cells replicates, but is not additive to, the protection afforded by ATL146e as assessed by serum alanine aminotransferase elevation, histological necrosis, neutrophil accumulation, and serum IFN-γ elevation. Reduced reperfusion injury observed in RAG 1 KO mice is restored to the WT level by adoptive transfer of NKT cells purified from WT or $A_{2A}R$ KO mice, but not IFN-γ KO mice. Additionally, animals with transferred $A_{2A}R^{-/-}$ NKT cells are not protected from hepatic reperfusion injury by ATL146e. In vitro, ATL146e potently inhibits both anti-CD3 and α-galactosylceramide-triggered production of IFN-γ by NKT cells. These findings suggest that hepatic reperfusion injury is initiated by the CD1d-dependent activation of NKT cells, and the activation of these cells is inhibited by $A_{2A}R$ activation.

Blockade of NKT Cell Activation Reduces Hepatic IRI

Figure 2A:
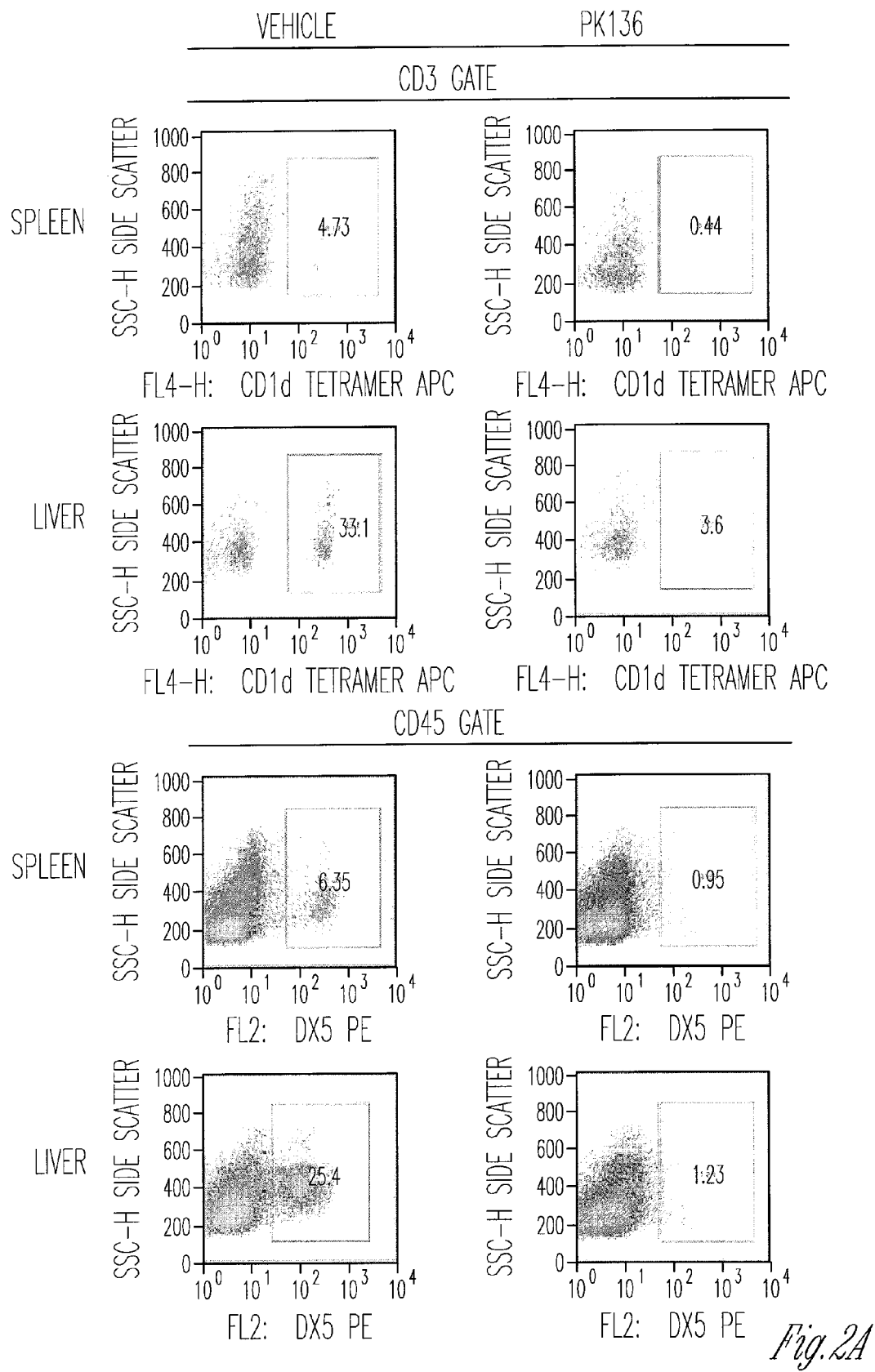
FIGS. 2A-C. Involvement of NKT in the pathogenesis of hepatic IRI. WT C57BL/6 mice were subjected to hepatic IRI or sham surgeries. Immediately after the initiation of reperfusion select animals received ATL146e or vehicle control. Additionally, animals received either a single i.p. injection of 200 μg PK136 or vehicle control two days prior to surgery (A and B) or a single i.p. injection of 300 μg of a CD1d blocking Ab or vehicle control 24 hours prior to surgery (C). Animals were sacrificed by cervical dislocation after 24 hours of reperfusion, blood was collected via retro-orbital bleed and serum ALT was measured. Livers were perfused and left liver lobes were collected and placed immediately into 4% paraformaldehyde. Necrosis was measured via H and E staining. Cell depletion by PK136 was assessed via the FACS analysis of spleen and liver tissue harvested from PK136-treated mice after 24 hours of reperfusion (A). Data shown are from three independent experiments (N=9); error bars indicate SEM. *p<0.01 vs. vehicle control as assessed by one way ANOVA followed by Dunnetts multiple comparison test. H and E staining shown is representative of 5 10× fields of view photographed for each of nine animals in three independent experiments.
Figure 2B:
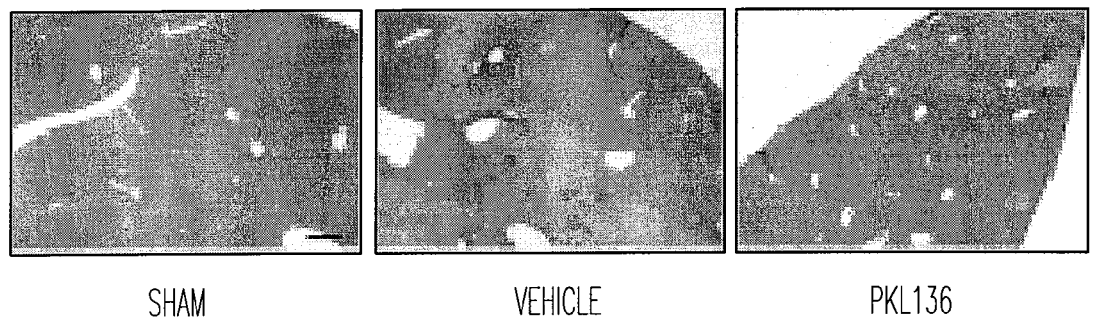
Figure 2B:
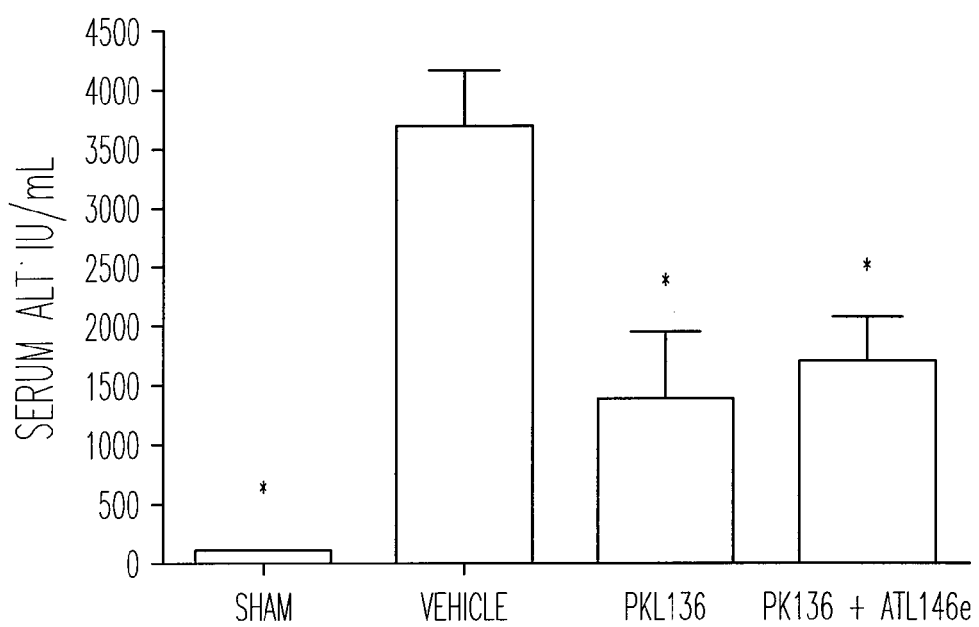
Figure 2C:
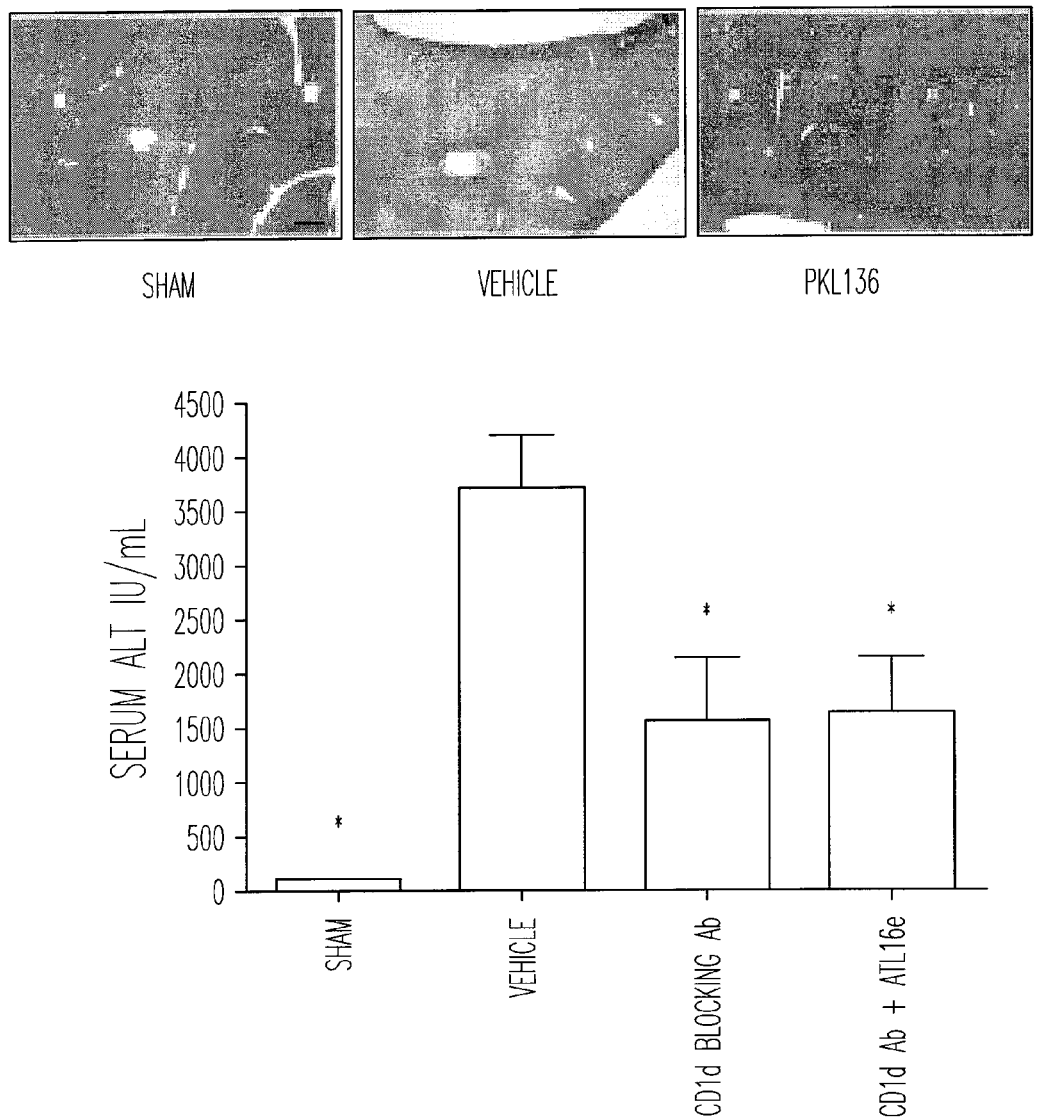

Clamping the hepatic triad of WT C57BL/6 mice for various times and reperfusing for 24 hours induces significant time-dependent liver damage. Deletion of the $A_{2A}R$ exacerbates reperfusion injury, implicating endogenous adenosine in liver protection[1]. Protection, as manifested by reduced serum alanine aminotransferase (ALT) levels and lessened necrotic area, is produced in WT mice by administration of the synthetic $A_{2A}R$ agonist, ATL146e, immediately after the initiation of reperfusion. Serum ALT levels in ATL146e-treated mice are reduced by approximately 58% versus vehicle treated controls, and necrotic area is 6.1±0.8% as opposed to 79.3±3% in vehicle treated animals (FIG. 1A; lightly stained areas are necrotic). RAG 1 KO mice, which lack mature lymphocytes, also exhibit reduced ALT and necrosis when compared to age and sex-matched WT C57BL/6 mice (63% reduction in serum ALT levels and 4.5±1% necrotic area) (FIG. 1B). ATL146e treatment of C57BL/6 mice and lymphocyte deficiency in RAG 1 KO mice result in similar reductions in serum ALT levels and liver necrosis. To test the hypothesis that NKT cell activity contributes to liver IR injury, we examined the effects of depleting these cells or blocking their CD1d-dependent activation. Treatment of WT C57BL/6 mice with anti-NK1.1 (PK136) two days prior to liver IRI substantially depletes NKT and NK cells in the spleen and liver as assessed by FACS analysis (FIG. 2A), while leaving conventional $CD4^+$ T cell and $CD8^+$ T cell number intact (data not shown). This depletion results in an approximate 60% reduction in serum ALT levels 24 hours after reperfusion and a large reduction in necrotic area (8.2±2% necrotic area) (FIG. 2B). The administration of a CD1d blocking Ab 24 hours before injury elicits a similar reduction in serum ALT levels and necrosis as does PK136 treatment (FIG. 2C). Co-treatment with either antibody in conjunction with ATL146e affords no additional protection beyond that achieved by NK1.1-cell depletion or CD1d blockade alone. These results are consistent with CD1d-restricted NKT cell involvement in hepatic IRI.

The Adoptive Transfer of NKT Cells Restores Liver Injury to RAG 1 KO Mice

Figure 3B:
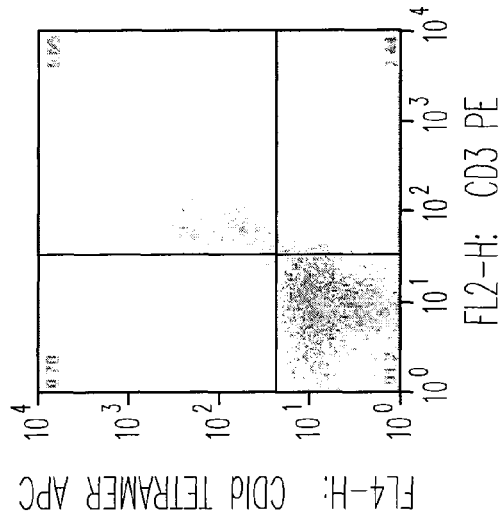
FIGS. 3A-D. Adoptive transfer of NKT cells restores injury to RAG 1 KO mice. WT or RAG 1 KO C57BL/6 mice were subjected to 72 minutes of hepatic IRI or sham surgeries. Immediately after the initiation of reperfusion select animals received ATL146e or vehicle control. Purified $CD4^+NK1.1^+$ T cells from WT (A and B), IFN-γ KO (C) or $A_{2A}R$ KO (D) C57BL/6 mice were adoptively transferred into select RAG 1 KO mice four days prior to hepatic IRI. Successful reconstitution of $CD4^+NK1.1^+$ T cells into the livers of recipient animals was confirmed by FACS analysis of leukocytes collected from liver tissue after 24 hours of reperfusion (B). Animals were sacrificed by cervical dislocation after 24 hours of reperfusion, blood was collected via retro-orbital bleed and serum ALT was measured. Data shown are from three independent experiments (N=9); error bars indicate SEM. *p<0.01 vs. WT C57BL/6 control as assessed by one way ANOVA followed by Dunnetts multiple comparison test.
Figure 3A:
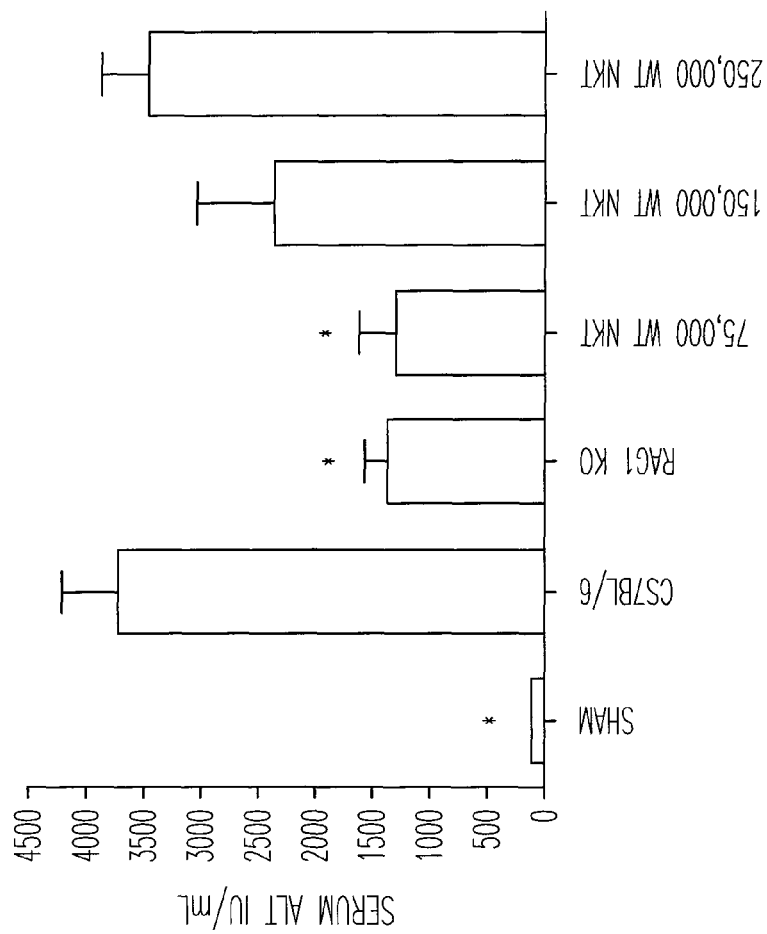
Figure 3D:
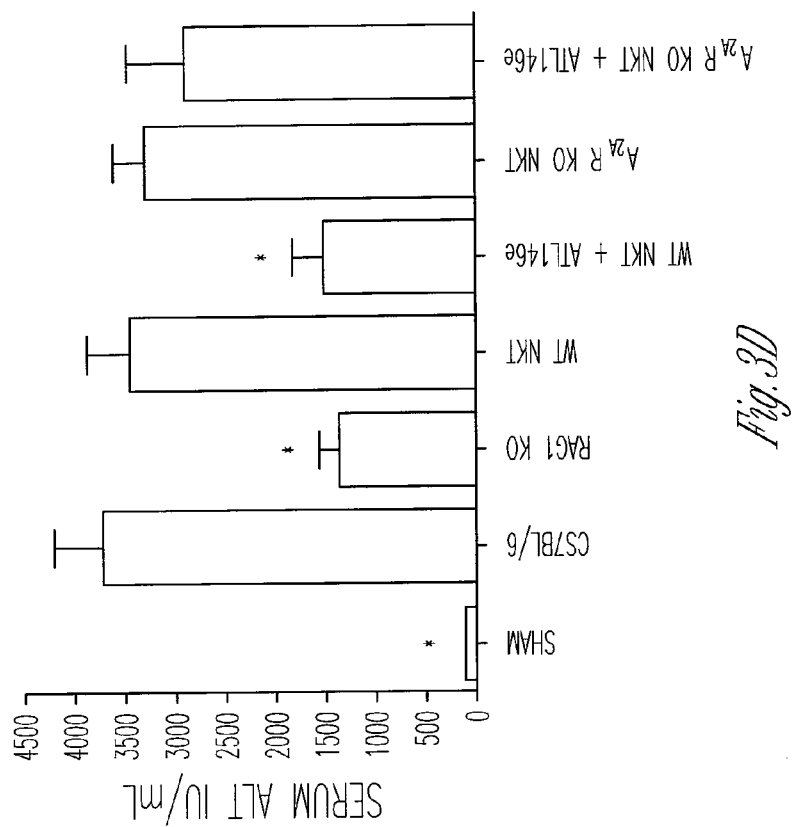
Figure 3C:
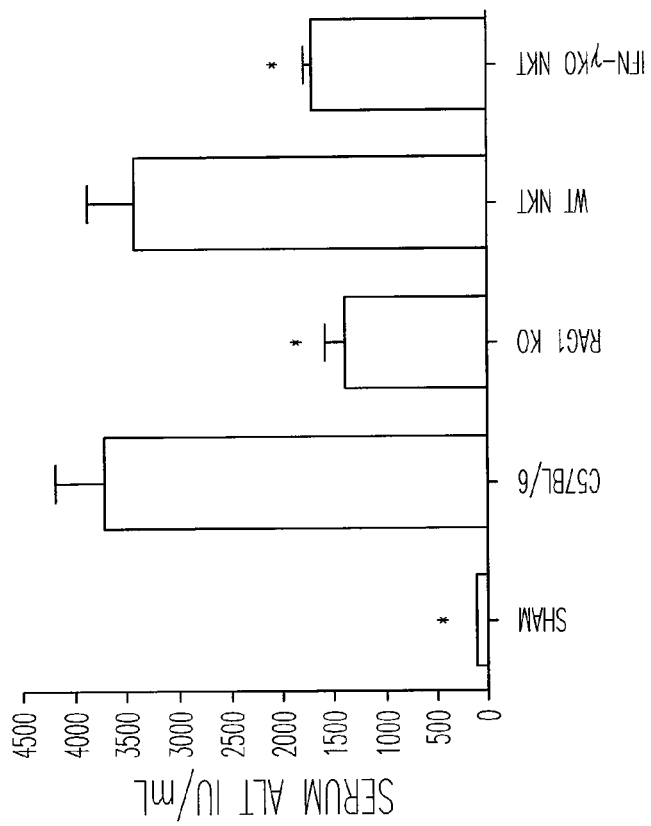

Adoptive transfer of $CD4^+$ $NK1.1^+$NKT cells collected from the spleens of WT C57BL/6 mice into RAG 1 KO mice four days before surgery was found to reconstitute hepatic injury after IRI. This effect is cell number-dependent, with WT levels of injury restored by the adoptive transfer of 250,000 NKT cells and intermediate injury by 150,000 cells (FIG. 3A). Approximately 75% of the $CD4^+NK1.1^+$ cells transferred expressed the invariant Vα14Jα18 TCR as indicated by binding of an α-Gal-Cer-loaded CD1d tetramer (data not shown), and FACS analysis confirmed that the adoptively transferred NKT cells reach the livers of reconstituted animals (FIG. 3B). Whereas the adoptive transfer of WT NKT cells reconstitutes liver injury after IRI, the transfer of 250,000 NKT cells collected from IFN-γ KO mice fails to do so; serum ALT levels are not significantly different from RAG 1 KO controls (FIG. 3C). The adoptive transfer of 250,000 NKT cells from $A_{2A}R$ KO mice restores injury to RAG 1 KO mice to an extent similar to transfer of WT NKT cells, but treatment with ATL146e protects from tissue damage only when WT cells are transferred; $A_{2A}R$ receptor deletion on the NKT cells abolishes the effect of agonist administration (FIG. 3D). These findings suggest that NKT cells play a pivotal role in hepatic reperfusion injury, that this activity is dependent upon the production of IFN-γ, and that the protection elicited by ATL146e treatment is dependent upon the expression of functional $A_{2A}$Rs on NKT cells IFNγ Production and Neutrophil Accumulation after Hepatic IRI is Dependent on NKT Cell Activation.

Figure 4A:
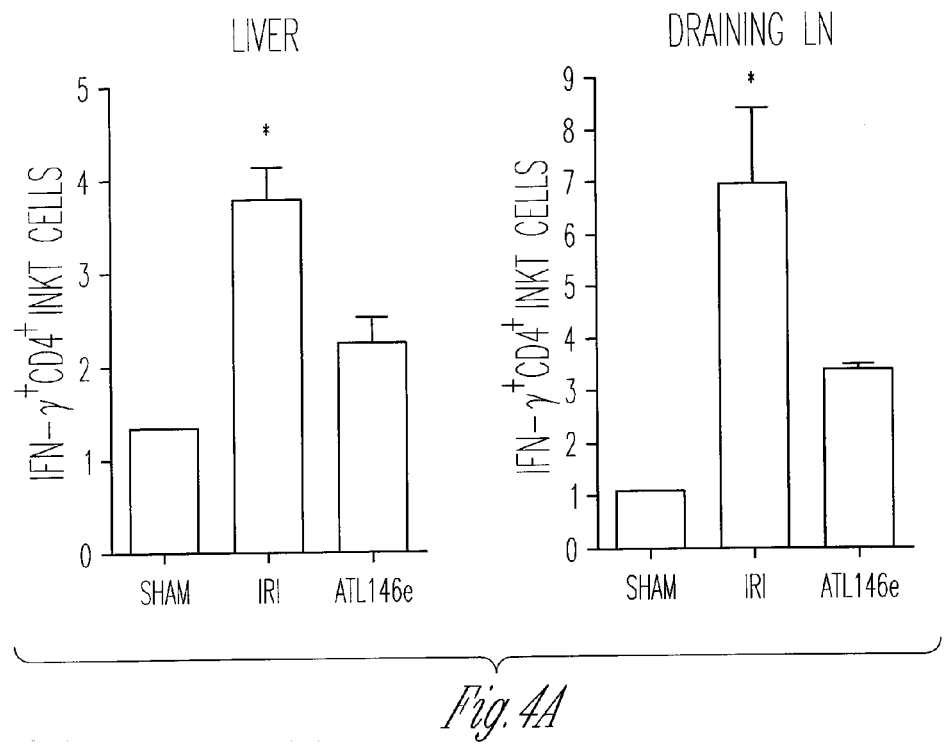
FIGS. 4A-C. Effect of NKT cell depletion or blockade on downstream events in reperfusion injury. WT or Rag1 KO C57BL/6 mice were subjected to 72 minutes of partial hepatic ischemia and 2 or 24 hours of reperfusion. Select animals received an i.p. injection of 200 μg PK136 2 days before surgery, an i.p. injection of 300 μg CD 1d blocking Ab 24 hours before surgery, or ATL146e immediately after the initiation of reperfusion. A) Intracellular IFN-γ production by $CD3^+/CD4^+/CD1d$-tetramer labeled NKT cells collected from post-ischemic tissue was assessed by FACS. Data shown are from three independent experiments (N=9); error bars indicate SEM. *p<0.05 vs. vehicle control as assessed by one way ANOVA followed by Dunnetts multiple comparison test. B) Blood was collected by retro-orbital bleed 24 hours after the initiation of reperfusion and serum IFN-γ levels were measured by ELISA. Data shown are from three independent experiments (N=9); error bars indicate SEM. *p<0.01 vs. vehicle control as assessed by one way ANOVA followed by Dunnetts multiple comparison test. C) Mice were sacrificed by cervical dislocation 24 hours after the initiation of reperfusion, livers were perfused and the left liver lobes were collected and placed immediately into 4% paraformaldehyde fixative. Immunostaining of neutrophils was performed with rat anti-mouse neutrophil primary antibody. Data shown are from a single experiment representative of three independent experiments (N=9).
Figure 4B:
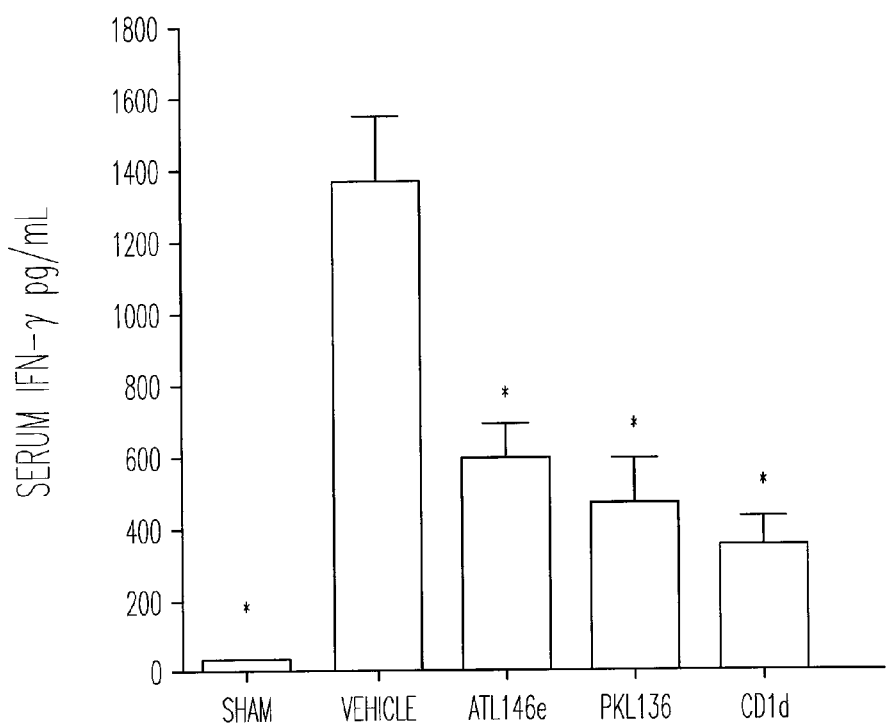
Figure 4C:
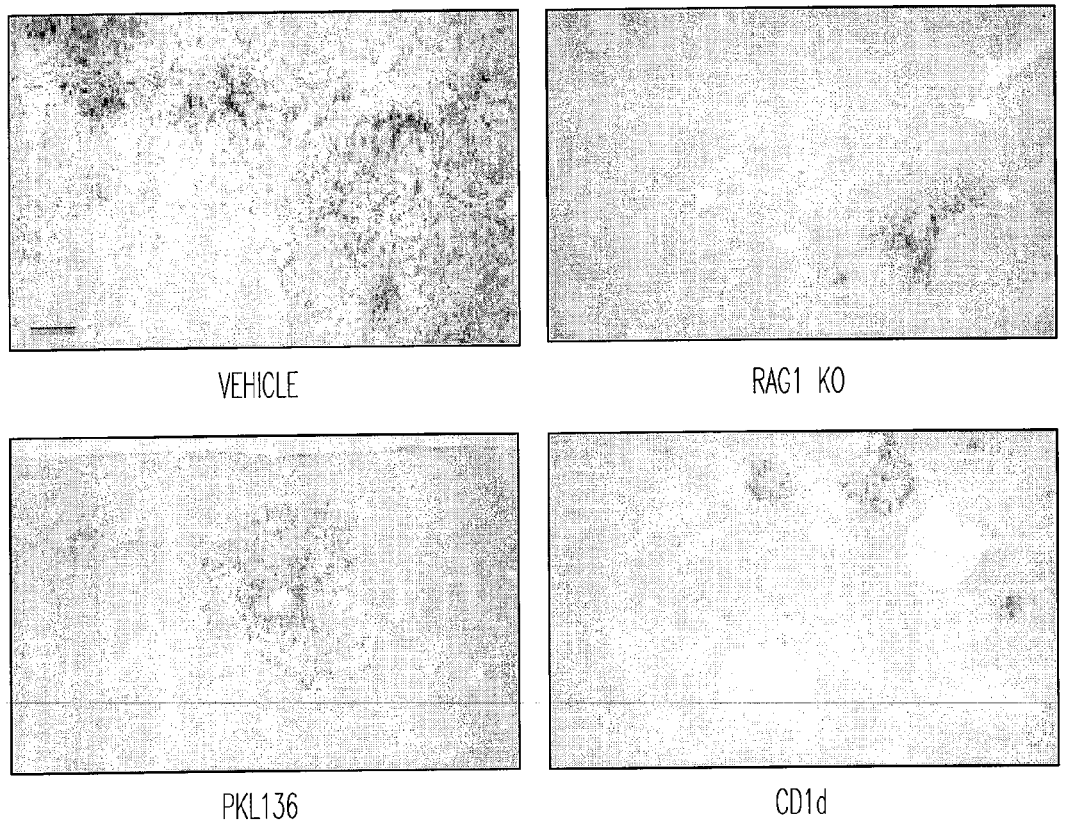

NKT cells isolated from post-ischemic mouse liver and liver-draining lymph nodes after 2 hours of reperfusion display an activated phenotype as indicated by an increase in intracellular IFN-γ expression as compared to sham surgery controls. Treatment with ATL146e at the initiation of reperfusion significantly inhibits this activation. (FIG. 4A). Because activated NKT cells are known to release large amounts of IFN-γ and to stimulate IFN-γ release from bystander cells, plasma levels of IFN-γ 24 hours after reperfusion injury were also examined. IRI substantially increased plasma IFN-γ concentrations at 24 hours, and treatment with ATL146e, PK136, or anti-CD1d antibodies all diminished this elevation to a similar extent (FIG. 4B). The large accumulation of neutrophils that is observed in the post-ischemic liver of WT C57BL/6 mice after 24 hours of reperfusion was also reduced significantly in RAG 1 KO mice, and to a similar extent in mice pre-treated with PK136 or CD1d blocking Ab (FIG. 4C). These findings indicate that NKT cells are activated rapidly after the initiation of reperfusion, that ATL146e inhibits this activation, and that the large accumulation of both serum IFN-γ and hepatic neutrophils that occurs 24 hours after liver reperfusion is secondary to NKT cell activation.

ATL146e Treatment Inhibits IFN-γ Production by Purified NKT Cells

Figure 5A:
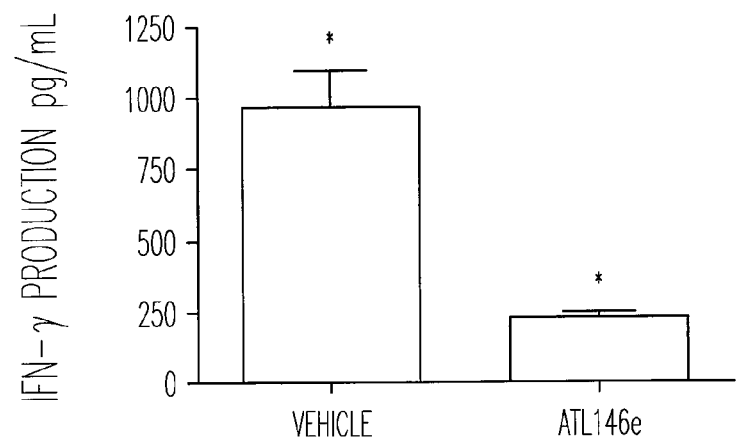
FIGS. 5A-E. Inhibition by ATL146e of IFN-γ production by activated NKT cells. A) Purified NKT cells (200,000 per well) were incubated on immobilized anti-CD3 mAb in the presence of vehicle or 100 nM ATL146e. Supernatants were collected after 24 hours and IFN-γ concentrations were measured by ELISA. Data are shown as the mean±SEM from three independent experiments performed in triplicate. *p<0.01 vs. vehicle control as assessed by unpaired t-test B) Bulk splenocytes (300,000 cells per well) were incubated with 1 U/mL ADA and 1 nM-1 μM α-galactosylceramide in the presence of 100 nM ATL146e or vehicle. C) Bulk splenocytes (300,000 cells per well) were incubated with 1 U/mL ADA and 1 μM α-galactosylceramide in the presence or absence of varying concentrations of ATL146e±100 nM ZM241385 or vehicle. D) Bulk splenocytes (300,000 cells per well) were incubated with 1 U/mL ADA and 1 μM α-galactosylceramide in the presence or absence of 1 nM ATL146e±1 μM 8-SPT or vehicle. E) Purified $CD4^+NK1.1^+$ T cells (150,000 cells per well) were incubated with lymphocyte and NK cell-deficient splenocytes (300,000 cells per well), 1 U/mL ADA and 1 μM α-galactosylceramide in the presence or absence of 100 nM ATL146e±100 nM ZM241385. NK1.1-expressing cells were depleted from RAG 1 KO splenocytes via FACSVantage SE Turbo Sorter. Supernatants were collected after 48 hours, and IFN-γ concentrations were determined by ELISA. Data shown are from a single experiment performed in triplicate, representative of three independent experiments; error bars indicate SEM. (B-E)*p<0.01 vs. vehicle control as assessed by one way ANOVA followed by Dunnetts multiple comparison test.
Figure 5B:
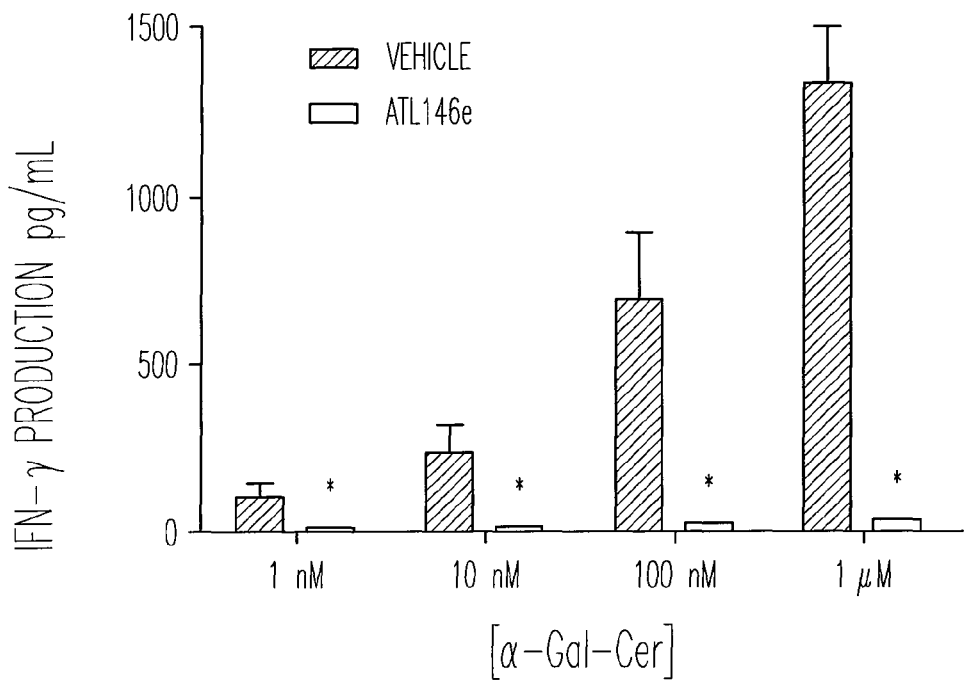
Figure 5C:
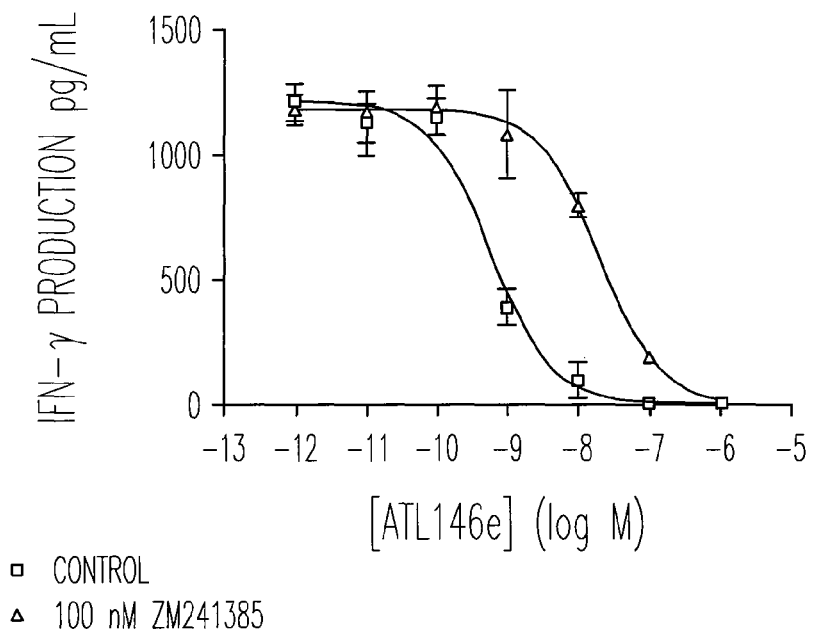
Figure 5D:
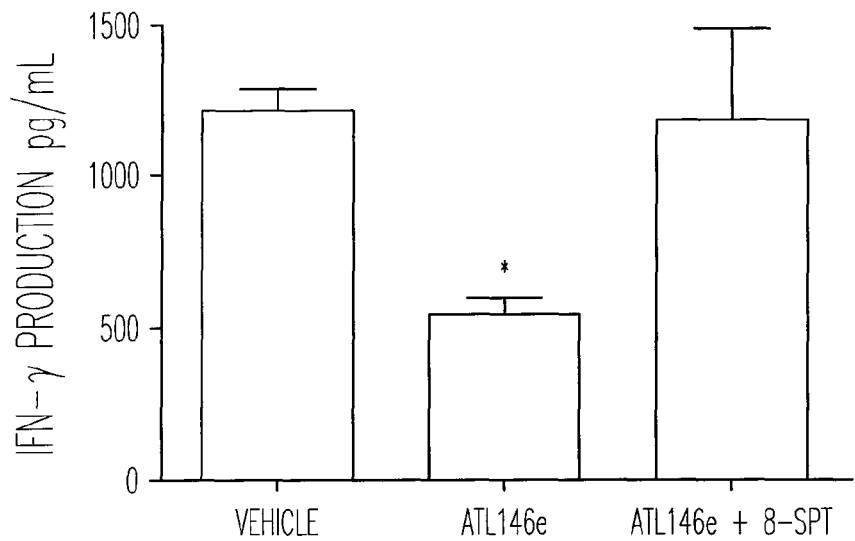
Figure 5E:
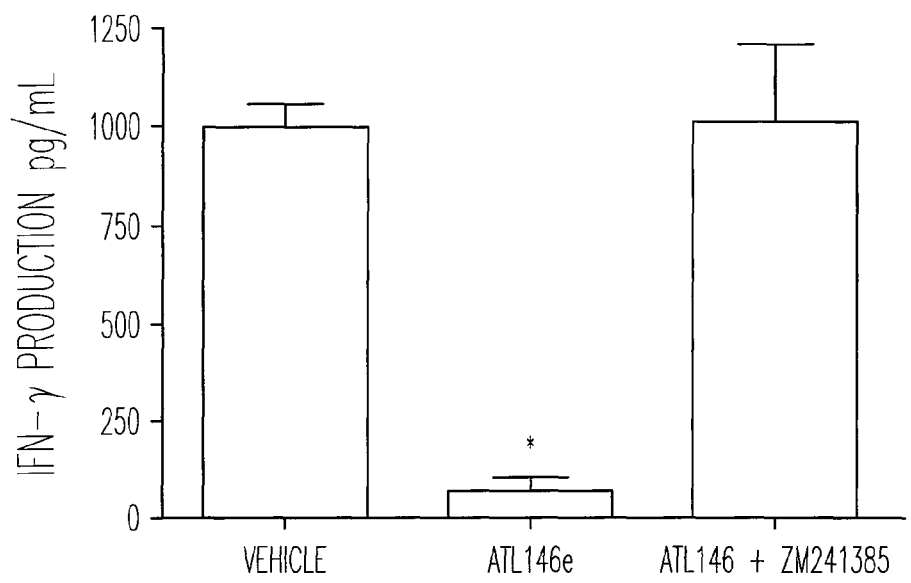

CD4+ NK1.1+NKT cells purified from spleens of WT C57BL/6 mice were activated on immobilized anti-CD3 mAb to stimulate the release of IFN-γ, as measured in cell supernatants after 24 hours of incubation. TCR-stimulated IFN-γ production is inhibited by approximately 73% by co-incubation with 100 nM ATL146e (FIG. 5A). Invariant NKT cells in a mixed splenocyte culture were selectively activated in a dose-dependent manner by α-Gal-Cer, and this activation stimulated the production of IFN-γ, which is inhibited competently by 100 nM ATL146e (FIG. 5B). The iNKT-mediated production of IFN-γ that is stimulated by 1 μM α-Gal-Cer is inhibited by ATL146e with an $EC_{50}$ value of 0.58 nM. The addition of 100 nM of the selective $A_{2A}R$ antagonist, 4-(2-[7-amino-2-[2-furyl][1,2,4]triazolo[2,3-a][1,3,5]triazin-5-yl-amino]ethyl)phenol (ZM241385) causes a right shift in the ATL146e dose response curve that is characteristic of competitive $A_{2A}R$ blockade (FIG. 5C). Co-treatment with 1 μM of the charged sulfonic acid adenosine receptor antagonist 8-sulfophenyltheophylline (8-SPT) also blocks the inhibitory effects of ATL146e on α-Gal-Cer mediated IFN-γ production by a mixed splenocyte culture (FIG. 5D). Because 8-SPT cannot cross the cell membrane, this indicates that the effects of ATL146e are mediated by $A_{2A}Rs$ expressed on the cell surface. It is possible that some of the IFN-γ produced by mixed splenocytes might be derived from the trans-activation of conventional lymphocytes or NK cells secondary to NKT cell activation. To eliminate these possible sources of IFN-γ, we also measured the release of IFN-γ from purified CD4+ NK1.1+ NKT cells activated with 1 μM α-Gal-Cer in the presence of lymphocyte-deficient, NK cell-depleted RAG 1 KO splenocytes as a source of APCs. IFN-γ derived from NKT cell activation in this experiment was reduced 93% by 100 mM ATL146e, and this effect was blocked by co-treatment with 100 nM ZM241385 (FIG. 5E). These findings demonstrate for the first time that the production of IFN-γ by NKT cells in response to CD1d-dependent activation is inhibited by activation of the $A_{2A}R$. Blockade of ATL146e activity by ZM241385 and 8-SPT indicate that this activity is dependent upon functional cell surface expression of the $A_{2A}R$.

Ischemia-reperfusion injury is characterized by initial tissue damage during the ischemic period followed by progressive injury during the reperfusion period. Reperfusion is a trigger for the generation of reactive oxygen species, release of cytokines, induction of adhesion molecules on vascular endothelial cells, and the adhesion and extravasation of leukocytes into post-ischemic tissue. We and others have found that treatment with agonists of adenosine $A_{2A}$ receptors or depletion of CD4+ lymphocytes effectively reduces inflammatory processes and the amount of tissue damage that occurs during reperfusion[8;15-18]. Of the total tissue necrosis that occurs in models of heart, kidney, skin, and liver ischemia-reperfusion injury, 30-75% of the tissue injury occurs during reperfusion and can be prevented by treatment with adenosine $A_{2A}R$ agonists[19]. In the current study we show that the activation of NKT cells by a CD1d-dependent mechanism plays a central role in initiating the inflammatory cascade responsible for reperfusion injury in the liver and that these cells are key targets of $A_{2A}R$ agonists (FIG. 6). Based upon adoptive transfer experiments of NKT cells into RAG 1 KO mice, we show that NKT cells are sufficient to cause reperfusion injury even in the absence of other lymphocytes. Additionally, we show that the activity of NKT cells to mediate liver reperfusion injury is dependent upon the production of IFN-γ, and that activation of the Gs-coupled $A_{2A}R$ markedly inhibits the production of IFN-γ by NKT cells both in vitro and in vivo. Although cAMP elevation has been found to inhibit CD8+ NKT cell cytotoxic activity[20], the current study is the first to demonstrate inhibition of CD4+ NKT cell cytokine production by a cAMP-elevating $A_{2A}R$ agonist.

Liver resident NKT cells are known to play a role in tumor surveillance and protection from hepatitis B viral infection[12; 21-23]. The selective activation of NKT cells with i.p. or i.v. injection of α-Gal-Cer results in an elevation of serum IFN-γ and ALT levels, and induces liver tissue damage[24]. The involvement of TCR activation in reperfusion injury is supported by previous work demonstrating that blockade of TCR signaling with cyclosporine treatment reduces hepatic reperfusion injury[25;26]. Additionally, CD1d−/− mice demonstrate significantly reduced liver reperfusion injury as compared to WT controls[27]. The activity of CD1d to activate NKT cells during reperfusion implicates host glycolipid antigens, possibly derived from or released from necrotic cells, in the rapid activation of the innate immune system. When activated, NKT cells rapidly release large amounts of both IL-4 and IFN-γ, which has been demonstrated to act via a STAT-1-dependent mechanism to activate Kupffer cells, as well as hepatocytes and sinusoidal endothelial cells, to produce chemokines and upregulate adhesion molecules responsible for promoting the infiltration of leukocytes[28]. IFN-γ also induces the generation of ROS and endoplasmic reticulum stress proteins in hepatocytes[29]. Although mediators such as FasL have been shown to play a role in lymphocyte-mediated liver injury[30;31], we show that NKT cell initiated reperfusion injury is dependent upon the production of IFN-γ. Whereas it is unlikely that conventional CD4+ T lymphocytes release large amounts of IFN-γ rapidly after exposure to activating stimuli, this is a characteristic response of CD4+ NK1.1+ NKT cells[32;33], and we show that NKT cells in the liver and liver draining lymph nodes have been stimulated to produce IFN-γ by 2 hours after the initiation of reperfusion. Moreover, the murine liver contains more NKT cells than any other immune organ[14], and based on these considerations and the data shown in this study, we propose that liver reperfusion injury results from an inflammatory cascade initiated by the release of IFN-γ from NKT cells. This in turn may stimulate the release of TNF-α and other cytokines from Kupffer cells, driving chemotaxis and activation of neutrophils, culminating in secondary liver injury (FIG. 6).

The C-type lectin receptor, NK1.1, is expressed on NKT cells and NK cells[34] and both cell types can be depleted competently by anti-NK1.1 antibodies as assessed by FACS analysis of splenocytes and liver leukocytes. The protective effect of PK136, therefore, indicates that NK cells, NKT cells, or both are involved in tissue damage after IRI. CD1d, however, acts specifically to prevent glycolipid antigen presentation to NKT cells[35], so the observation that the blockade of CD1d protects from hepatic IRI to a similar extent as does PK136 treatment indicates that NKT cells are the NK1.1-expressing cell type predominantly responsible for the induction of reperfusion injury. It is possible, however, that NK cells are involved in the later stages of injury owing to their trans-activation by NKT-cell released cytokines[36;37]. Prior studies have implicated T cells in reperfusion injury, but a T cell-activating stimulus has not previously been clearly identified. Our data implicate CD1d-dependent antigen presentation as an early event in the inflammatory cascade, but it may not be the only stimulus. $H_2O_2$ derived from ROS is produced early during reperfusion and is known to facilitate activation of T cells through the oxidation of cysteine residues on protein tyrosine phosphatases that dephosphorylate activated TCRs[38;39]. In addition, $H_2O_2$ directly activates NF-κB40 resulting in widespread activation of inflammatory cells. Thus, NKT cell activation and ROS may collaborate to trigger reperfusion injury.

The results of this study implicate NKT cells as predominant mediators of hepatic reperfusion injury that are sensitive to regulation by $A_{2A}R$ activation. Residual injury that is observed after blockade of NKT activation may be due to damage caused in an inflammatory cell-independent manner during the ischemic period. The majority, but not all, mouse CD4+ NK1.1+ NKT cells express an invariant Vα14Jα18 TCR, and we show that these cells are activated to produce IFN-γ early after the initiation of reperfusion. Moreover, this activation is inhibited by ATL146e treatment, resulting in substantial protection from injury. These data suggest that Vα14Jα18 iNKT cells play a role in reperfusion injury. Nevertheless, there are CD1d dependent murine NKT cells with diverse TCRs that may also be activated during reperfusion injury if CD1d-dependent ligands for these cells are generated. Protection from iNKT-cell mediated injury by $A_{2A}R$ activation may be relevant in humans since an analogous Vα24 NKT cell population exists[41] and these cells and similar cells in other mammalian species are activated by glypolipid antigens[42]. Interestingly, a sub-population of CD1-reactive, non-invariant NKT cells have been identified in human liver[43]. These intrahepatic cells are Th1 polarized and display similar activity as their invariant counterparts. It is feasible that if the reduced numbers of iNKT cells found in human liver are insufficient to induce hepatic injury after reperfusion, the specialized sub-set of CD1-restricted non-invariant NKT cells may be poised to act in their stead or in addition to invariant cells. Human NKT cells have been implicated in the pathophysiology of primary biliary cirrhosis suggesting that these cells are physiologically important in man[44].

The results of this work suggest a paradigm shift in the way we view the role of T lymphocytes in ischemia reperfusion injury. Whereas myeloid cells have previously been thought of as the major facilitators of reperfusion injury, the current study indicates that the initiation of the reperfusion-induced inflammatory cascade is dependent upon CD1d-mediated IFN-γ production by NKT cells. Furthermore, profound protection is imparted when this early event in the inflammatory cascade is inhibited by $A_{2A}R$ activation, and through this mechanism, the release of adenosine from injured tissue may serve as an endogenous regulator of NKT cell activity. Clinicians have historically attempted to limit the by-products of reperfusion induced inflammation via the use of neutralizing antibodies to cytokines or free radical scavengers, but it may be possible to reduce the production of these mediators more significantly by targeting an upstream event in the cascade-namely NKT cell activation. The activities of ATL146e to potently inhibit the production of IFN-γ by CD1d-activated NKT cells, and to dramatically protect the liver from reperfusion injury, indicate that $A_{2A}R$ selective agonists may be useful tools in the treatment of IRI. Moreover, there is no evidence of severe toxicity evoked by the use of $A_{2A}R$ agonists as anti-inflammatory agents.

It is understood that any embodiment or feature of the present invention whether characterized as preferred or not characterized as preferred may be combined with any other embodiment or feature of the invention, whether such other feature is characterized as preferred or not characterized as preferred.

The terms "include", "for example", "such as", and the like are used illustratively and are not intended to limit the present invention.

The indefinite articles "a" and "an" mean "at least one" or "one or more" when used in this application, including the claims, unless specifically indicated otherwise.

Mammal and patient covers warm blooded mammals that are typically under medical care (e.g., humans and domesticated animals). Examples of mammals include (a) feline, canine, equine, bovine, procine, and human and (b) human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Therapeutically effective amount" includes an amount of a compound of the present invention that is effective when administered alone or in combination to a indication listed herein. "Therapeutically effective amount" also includes an amount of the combination of compounds claimed that is effective to treat the desired indication. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

Specific and preferred values listed for radicals, substituents, and ranges, are for illustration only; they do not exclude other defined values or other values within defined ranges for the radicals and substituents.

The present agents may be systemically administered, e.g., orally, in combination with a pharmaceutically acceptable excipient such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active agent may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with several of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508). Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from (a) about 0.1-25 wt % and (b) about 0.5-10 wt %. The concentration in a semi-solid or solid composition such as a gel or a powder will be (a) about 0.1-5 wt % and (b) about 0.5-2.5 wt %.

The amount of the agent required for use in treatment will vary not only with the particular agent selected but also with the route of administration, the nature of the condition being treated, and the age and condition of the patient and will be ultimately at the discretion of the attendant physician or clinician. In general, however, a suitable dose will be in the range of from (a) about 1.0-100 mg/kg of body weight per day, (b) about 10-75 mg/kg of body weight per day, and (c) about 5-20 mg per kilogram body weight per day.

The agent may be conveniently administered in unit dosage form; e.g., tablets, caplets, etc., containing (a) about 4-400 mg, (b) about 10-200 mg, and (c) about 20-100 mg of active ingredient per unit dosage form.

Ideally, the active ingredient should be administered to achieve peak plasma concentrations of the active compound of from (a) about 0.02-20 μM, (b) about 0.1-10 μM, and (c) about 0.5-5 μM. These concentrations may be achieved, for example, by the intravenous injection of a 0.005-0.5% solution of the active ingredient, or orally administered as a bolus containing about 4-400 mg of the active ingredient.

The agents of the invention may also be administered by inhalation from an inhaler, insufflator, atomizer or pressurized pack or other means of delivering an aerosol spray. Pressurized packs may comprise a suitable propellant such as carbon dioxide or other suitable gas. In case of a pressurized aerosol, the dosage unit may be determined by providing a value to deliver a metered amount. The inhalers, insufflators, atomizers are fully described in pharmaceutical reference books such as Remington's Pharmaceutical Sciences Volumes 16 (1980) or 18 (1990) Mack Publishing Co.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

All patents, patent applications, books and literature cited in the specification are hereby incorporated by reference in their entirety. In the case of any inconsistencies, the present disclosure, including any definitions therein will prevail.

The invention has been described with reference to various specific and preferred embodiments and techniques. However, it should be understood that many variations and modifications may be made while remaining within the spirit and scope of the invention.

EXAMPLES

Materials and Methods

Animals

Wild-type, RAG 1 KO and IFN-γ KO C57BL/6 mice were purchased from Jackson Laboratories. $A_{2A}R$ KO mice on a mixed genetic background were provided by Dr. Jiang-Fan Chen of Boston University. All animal studies were approved by the University of Virginia Animal Care and Use Committee.

Creating $A_{2A}R$ KO Mice Congenic to C57BL/6

The KO locus of B6; 129P-adora2a$^{tm1chen}$ mice with an ablated $A_{2A}R$ gene on a mixed genetic background[45] was moved onto a C57BL/6 background by monitoring 96 microsatellites for 5 generations of marker-assisted breeding. In the resulting mouse line, DNA derived from the 129 strain can be detected only in an 8 cM region between D10Mit31 and D10Mit42 surrounding the Adora2a locus on chromosome 10.

NKT Cell Purification

Wild-type, $A_{2A}R$ KO, or IFN-γ KO C57BL/6 mice were sacrificed and spleens removed. Splenocytes were passed through a 40 μm nylon cell strainer (BD Biosciences, San Jose, Calif.) and collected in phosphate buffered saline. Red blood cells were lysed and CD4$^+$ T lymphocytes were isolated with mouse CD4 subset column kits (R and D Systems, Minneapolis, Minn.) resulting in >92% pure CD4$^+$ T cells. The column-purified cells were stained for 30 minutes with FITC-conjugated anti-mouse CD4 and PE-conjugated anti-mouse NK1.1 (eBioscience, San Diego, Calif.) and sorted using a FACSVantage SE Turbo Sorter (Becton Dickinson, Franklin Lakes, N.J.) to produce cell populations of ≧99.8% pure CD4$^+$NK1.1$^+$ T lymphocytes.

In Vitro Activation of NKT Cells

Cells were washed and resuspended in RPMI 1640 medium supplemented with 10% heat-inactivated fetal bovine serum and 1% antibiotic-antimycotic (Gibco, Carlsbad, Calif.). In vitro activation of NKT cells was achieved by co-culture for 48 hours with splenocytes and 1 nM-1 μM α-Gal-Cer (KRN7000; from Kumi Miyayama of Kirin Brewery Company, Tokyo) at 37° C. in 5% $CO_2$. Alternately, NKT cells were activated by incubation for 24 hours in 96 well plates coated with 2-10 μg/mL immobilized anti-CD3 mAb (BD Biosciences) at 37° C. in 5% $CO_2$. All in vitro T cell activation experiments were performed with the addition of 1 U/mL adenosine deaminase (ADA) (Roche, Indianapolis, Ind.) to remove endogenous adenosine produced by the cells that may partially activate the $A_{2A}R$. For select experiments cells were co-cultured with ATL146e (from Jayson Rieger of Adenosine Therapeutics, Charlottesville, Va.) in the presence or absence of 100 nM of the selective $A_{2A}R$ antagonist, ZM241385 (Tocris, Ellisville, Mo.), or 1 μM of the cell-impermeable AR antagonist, 8-SPT (Research Biochemicals International, Natick, Mass.).

Hepatic Ischemia Reperfusion Injury

Mice were anesthetized by intraperitoneal injection of ketamine (100 mg/kg) and xylazine (10 mg/kg). Ambient temperature was controlled in the range of 24-26° C. and mice were placed on a 37° heating pad. Core body temperature of selected mice was monitored with a TH-8 Thermalert monitoring thermometer (Physitemp) and ranged from 35-36°. After midline laparotomy, a microaneurysm clip was applied to the hepatic triad above the bifurcation to clamp the flow of the hepatic artery, portal vein, and bile duct. After superfusion of the liver with warm saline, the peritoneum was closed during 72 min of ischemia. The peritoneum was then reopened and the microaneurysm clip was removed. For select experiments, animals received an i.p. loading dose (1 μg/kg) of ATL146e or vehicle control immediately after the onset of reperfusion, and a primed Alzet osmotic minipump was implanted intraperitoneally. ATL146e (10 ng/kg/min) or vehicle was placed in the pumps and delivered until the experiment was terminated. The peritoneum was sutured and the surgical wound was closed with metal staples. Animals were sacrificed by cervical dislocation at various time points after the initiation of reperfusion and blood was collected via retro-orbital bleed. Additionally, livers were perfused and left liver lobes were collected.

NK1.1 Cell Depletion and CD1d Blockade

NK1.1-expressing cells were depleted via a single i.p. injection of 200 μg PK136[46] (a gift from Dr. Michael Brown, University of Virginia, Charlottesville, Va.) two days before hepatic IRI. Successful depletion was confirmed by FACS analysis of splenocytes and liver leukocytes collected at the termination of reperfusion. CD1d was blocked by a single i.p. injection of 300 μg of anti-mouse CD1d mAb clone 1B1[47] (a gift from Dr. Mitchell Kronenberg, La Jolla Institute for Allergy and Immunology, San Diego, Calif.) 24 hours before hepatic IRI. Anti-NK1.1 (PK136) and anti-CD1d (clone 1B1) were purified from hybridomas in the University of Virginia hybridoma core (Charlottesville, Va.).

Adoptive Transfer of NKT Cells

CD4$^+$ NK1.1$^+$ NKT cells were purified from WT, $A_{2A}R$ KO, or IFN-γ KO C57BL/6 mice and adoptively transferred into RAG 1 KO mice via jugular vein injection 4 days prior to hepatic IRI. Successful reconstitution was confirmed by FACS analysis. Control animals received vehicle injections.

Serum Alanine Aminotransferase Determination

Following liver ischemia, blood was collected via retro-orbital bleed 24 hours after the initiation of reperfusion. Serum ALT was measured with a transaminase kit according to the manufacture's protocol (Pointe Scientific, Canton, Mich.). Briefly, 20 μL of undiluted or 10×-diluted serum was added to 200 μl of a preheated (37° C.) mix of L-alanine (500 mM) and α-ketoglutaric acid (15 mM) in a 96 well plate. The plate was placed in a spectrophotometer preheated to 37° C., and the absorbance at 304 nm was measured every minute for 10 minutes. The slope of the linear portion of the change in absorbance over time was used to calculate IU/L of ALT.

Flow Cytometry of Cell Surface T Cell Markers

Spleens were harvested, passed through a 40 μm nylon cell strainer (BD Biosciences) and collected in phosphate buffered saline. Red blood cells were lysed. Alternately, livers were harvested, passed through a 40 μm cell strainer and leukocyte fractions were isolated via Percol density gradient. Cells were washed and resuspended at 5×10$^6$ cells/mL in PBS supplemented with 5% FBS and 0.1% $NaN_3$. Aliquots (0.1 mL) were placed on ice and labeled for 30 minutes in the dark with anti-mouse CD45, anti-mouse CD3, anti-mouse CD4, anti-mouse CD8, anti-mouse NK1.1, anti-mouse CD49b (DX5), (eBioscience) and/or α-Gal-Cer-loaded CD1d tetramer (NIAID Tetramer Facility, Germantown, Md.). Control samples were labeled with isotype matched control antibodies. Stained cells were washed with 1 mL iced PBS and resuspended in PBS containing 1% paraformaldehyde. The fluorescence intensity was measured with a Becton Dickinson FACSCalibur dual laser benchtop flow cytometer with a minimum of 10,000 events being collected. An excitation wavelength of 488 nm and emission wavelength of 530 was used for FITC stained cells, an excitation wavelength of 488 nm and emission wavelength of 585 was used for PE stained cells, an excitation wavelength of 635 nm and emission wavelength of 661 was used for APC and Alexa 647 stained cells, and an excitation wavelength of 488 nm and emission wavelength of 670 was used for PE-Cy5.5 stained cells. Analysis was performed with FlowJo software; $CD45^+$ cells were gated on for analysis (Tree Star, Inc., Ashland, Oreg.).

Detection of Intracellular IFN-γ

Intracellular IFN-γ was detected in liver NKT cells by FACS analysis using Fix and Perm Cell Permeabilization Reagents according to the manufacturer's protocol (Caltag Laboratories, Carlsbad, Calif.).

Histology

Mice were sacrificed and livers perfused with saline via the portal vein at various times after the initiation of reperfusion. Left liver lobes were harvested, fixed in 4% paraformaldehyde in PBS, pH 7.4, and embedded in paraffin. Four-micrometer sections were subjected to standard hematoxylin and eosin staining. Necrotic area was quantified using Adobe Photoshop software.

Measurement of IFN-γ

IFN-γ concentrations in cell culture supernatants or serum samples were measured by ELISA according to the manufacturer's protocol (e-Bioscience).

Statistics

GraphPad Prism software was utilized for all statistical analyses. Unpaired t-tests or one way analysis of variance with post-hoc Dunnetts multiple comparison was used to compare experimental groups to a control group.

Acknowledgements: Anti-NK1.1 antibody, PK136, was a gift from Dr. Michael Brown of the University of Virginia, and anti-mouse CD1d mAb clone 1B1 was from Dr. Mitchell Kronenberg, La Jolla Institute for Allergy and Immunology, San Diego, Calif.

Abbreviations List:
α-Gal-Cer, a-galactosylceramide;
ADA, adenosine deaminase;
AR, adenosine receptor;
ALT, alanine aminotransferase
ATL146e, 4-{3-[6-Amino-9-(5-ethylcarbamoyl-3,4-dihydroxy-tetrahydro-furan-2-yl)-9H-purin-2-yl]-prop-2-ynyl}-cyclohexanecarboxylic acid methyl ester
IRI, ischemia reperfusion injury;
iNKT, invariant NKT;
8-SPT, 8-sulfophenyltheophylline; and,
ZM241385, 4-(2-[7-amino-2-[2-furyl][1,2,4]triazolo[2,3-a][1,3,5]triazin-5-yl-amino]ethyl)phenol.

BIBLIOGRAPHY

1. Day, Y. J., M. A. Marshall, L. Huang, M. J. McDuffie, M. D. Okusa, and J. Linden. 2004. Protection from ischemic liver injury by activation of A2A adenosine receptors during reperfusion: inhibition of chemokine induction. *Am. J. Physiol Gastrointest. Liver Physiol* 286:G285-G293.
2. Cronstein, B. N. 1994. Adenosine, an endogenous anti-inflammatory agent. *J. Appl. Physiol* 76:5-13.
3. Lappas, C. M., J. M. Rieger, and J. Linden. 2005. A2A adenosine receptor induction inhibits IFN-gamma production in murine $CD4^+$ T cells. *J. Immunol.* 174:1073-1080.
4. Linden, J. 2001. Molecular approach to adenosine receptors: receptor-mediated mechanisms of tissue protection. *Annu. Rev. Pharmacol. Toxicol.* 41:775-787.
5. Ohta, A. and M. Sitkovsky. 2001. Role of G-protein-coupled adenosine receptors in downregulation of inflammation and protection from tissue damage. *Nature* 414:916-920.
6. Sullivan, G. W., J. Linden, E. L. Hewlett, H. T. Carper, J. B. Hylton, and G. L. Mandell. 1990. Adenosine and related compounds counteract tumor necrosis factor-alpha inhibition of neutrophil migration: implication of a novel cyclic AMP-independent action on the cell surface. *J. Immunol.* 145:1537-1544.
7. Sullivan, G. W., J. M. Rieger, W. M. Scheld, T. L. Macdonald, and J. Linden. 2001. Cyclic AMP-dependent inhibition of human neutrophil oxidative activity by substituted 2-propynylcyclohexyl adenosine A(2A) receptor agonists. *Br. J. Pharmacol* 132:1017-1026.
8. Day, Y. J., Y. Li, J. M. Rieger, S. I. Ramos, M. D. Okusa, and J. Linden. 2005. A2A adenosine receptors on bone marrow-derived cells protect liver from ischemia-reperfusion injury. *J. Immunol.* 174:5040-5046.
9. Bendelac, A., M. N. Rivera, S. H. Park, and J. H. Roark. 1997. Mouse CD1-specific NK1 T cells: development, specificity, and function. *Annu. Rev. Immunol.* 15:535-562.
10. Godfrey, D. I., H. R. MacDonald, M. Kronenberg, M. J. Smyth, and K. L. Van. 2004. NKT cells: what's in a name? *Nat. Rev. Immunol.* 4:231-237.
11. Zhou, D., J. Mattner, C. Cantu, III, N. Schrantz, N. Yin, Y. Gao, Y. Sagiv, K. Hudspeth, Y. P. Wu, T. Yamashita, S. Teneberg, D. Wang, R. L. Proia, S. B. Levery, P. B. Savage, L. Teyton, and A. Bendelac. 2004. Lysosomal glycosphingolipid recognition by NKT cells. *Science* 306:1786-1789.
12. Kawano, T., J. Cui, Y. Koezuka, I. Toura, Y. Kaneko, H. Sato, E. Kondo, M. Harada, H. Koseki, T. Nakayama, Y. Tanaka, and M. Taniguchi. 1998. Natural killer-like nonspecific tumor cell lysis mediated by specific ligand-activated Valpha14 NKT cells. *Proc. Natl. Acad. Sci. U.S. A* 95:5690-5693.
13. Kronenberg, M. 2005. Toward an understanding of NKT cell biology: progress and paradoxes. *Annu. Rev. Immunol.* 23:877-900.
14. Hammond, K. J., D. G. Pellicci, L. D. Poulton, O. V. Naidenko, A. A. Scalzo, A. G. Baxter, and D. I. Godfrey. 2001. CD1d-restricted NKT cells: an interstrain comparison. *J. Immunol.* 167:1164-1173.
15. Day, Y. J., L. Huang, H. Ye, L. Li, J. Linden, and M. D. Okusa. 2006. Renal ischemia-reperfusion injury and adenosine 2A receptor-mediated tissue protection: the role of $CD4^+$ T cells and IFN-gamma. J. Immunol. 176:3108-3114.
16. Yang, Z., Y. J. Day, M. C. Toufektsian, S. I. Ramos, M. Marshall, X. Q. Wang, B. A. French, and J. Linden. 2005. Infarct-sparing effect of A2A-adenosine receptor activation is due primarily to its action on lymphocytes. *Circulation* 111:2190-2197.
17. Savransky, V., R. R. Molls, M. Bume-Taney, C. C. Chien, L. Racusen, and H. Rabb. 2006. Role of the T-cell receptor in kidney ischemia-reperfusion injury. *Kidney Int.* 69:233-238.
18. Yokota, N., F. Daniels, J. Crosson, and H. Rabb. 2002. Protective effect of T cell depletion in murine renal ischemia-reperfusion injury. *Transplantation* 74:759-763.
19. Linden, J. 2005. Adenosine in tissue protection and tissue regeneration. *Mol. Pharmacol.* 67:1385-1387.
20. Scheffold, C., M. Komacker, Y. C. Scheffold, C. H. Contag, and R. S. Negrin. 2002. Visualization of effective 20. tumor targeting by CD8+ natural killer T cells redirected with bispecific antibody F(ab')(2)HER2xCD3. *Cancer Res.* 62:5785-5791.
21. Grubor-Bauk, B., A. Simmons, G. Mayrhofer, and P. G. Speck. 2003. Impaired clearance of herpes simplex virus type 1 from mice lacking CD1d or NKT cells expressing the semivariant V alpha 14-J alpha 281 TCR. *J. Immunol.* 170:1430-1434.
22. Kakimi, K., L. G. Guidotti, Y. Koezuka, and F. V. Chisari. 2000. Natural killer T cell activation inhibits hepatitis B virus replication in vivo. *J. Exp. Med.* 192:921-930.
23. Smyth, M. J., K. Y. Thia, S. E. Street, E. Cretney, J. A. Trapani, M. Taniguchi, T. Kawano, S. B. Pelikan, N. Y. Crowe, and D. I. Godfrey. 2000. Differential tumor surveillance by natural killer (NK) and NKT cells. *J. Exp. Med.* 191:661-668.
24. Godfrey, D. I., K. J. Hammond, L. D. Poulton, M. J. Smyth, and A. G. Baxter. 2000. NKT cells: facts, functions and fallacies. *Immunol. Today* 21:573-583.
25. Kurokawa, T., H. Kobayashi, T. Nonami, A. Harada, A. Nakao, S. Sugiyama, T. Ozawa, and H. Takagi. 1992. Beneficial effects of cyclosporine on postischemic liver injury in rats. *Transplantation* 53:308-311.
26. Sakr, M. F. and A. N. bdel-Aal. 1996. Protective effect of cyclosporine A (CyA) against the hepatic injury associated with ischemia and reperfusion. *Int. Surg.* 81:180-183.
27. Shimamura, K., H. Kawamura, T. Nagura, T. Kato, T. Naito, H. Kameyama, K. Hatakeyama, and T. Abo. 2005. Association of NKT cells and granulocytes with liver injury after reperfusion of the portal vein. *Cell Immunol.* 234:31-38.
28. Jaruga, B., F. Hong, W. H. Kim, and B. Gao. 2004. IFN-gamma/STAT1 acts as a proinflammatory signal in T cell-mediated hepatitis via induction of multiple chemokines and adhesion molecules: a critical role of IRF-1. *Am. J. Physiol Gastrointest. Liver Physiol* 287:G1044-G1052.
29. Watanabe, Y., O. Suzuki, T. Haruyama, and T. Akaike. 2003. Interferon-gamma induces reactive oxygen species and endoplasmic reticulum stress at the hepatic apoptosis. *J. Cell Biochem.* 89:244-253.
30. Kondo, T., T. Suda, H. Fukuyama, M. Adachi, and S. Nagata. 1997. Essential roles of the Fas ligand in the development of hepatitis. *Nat. Med.* 3:409-413.
31. Li, M. and G. T. Liu. 2004. Inhibition of Fas/FasL mRNA expression and TNF-alpha release in concanavalin A-induced liver injury in mice by bicyclol. *World J. Gastroenterol.* 10:1775-1779.
32. Fujii, S., K. Shimizu, M. Kronenberg, and R. M. Steinman. 2002. Prolonged IFN-gamma-producing NKT response induced with alpha-galactosylceramide-loaded DCs. *Nat. Immunol.* 3:867-874.
33. Hansen, D. S, and L. Schofield. 2004. Regulation of immunity and pathogenesis in infectious diseases by CD1d-restricted NKT cells. *Int. J. Parasitol.* 34:15-25.
34. Mercer, J. C., M. J. Ragin, and A. August. 2005. Natural killer T cells: rapid responders controlling immunity and disease. *Int. J. Biochem. Cell Biol.* 37:1337-1343.
35. Yu, K. O. and S. A. Porcelli. 2005. The diverse functions of CD1d-restricted NKT cells and their potential for immunotherapy. *Immunol. Lett.* 100:42-55.
36. Carnaud, C., D. Lee, O. Donnars, S. H. Park, A. Beavis, Y. Koezuka, and A. Bendelac. 1999. Cutting edge: Cross-talk between cells of the innate immune system: NKT cells rapidly activate NK cells. *J. Immunol.* 163:4647-4650.
37. Eberl, G. and H. R. MacDonald. 2000. Selective induction of NK cell proliferation and cytotoxicity by activated NKT cells. *Eur. J. Immunol.* 30:985-992.
38. Ginn-Pease, M. E. and R. L. Whisler. 1998. Redox signals and NF-kappaB activation in T cells. *Free Radic. Biol. Med.* 25:346-361.
39. Reth, M. 2002. Hydrogen peroxide as second messenger in lymphocyte activation. *Nat. Immunol.* 3:1129-1134.
40. Majumdar, S., B. Lamothe, and B. B. Aggarwal. 2002. Thalidomide suppresses NF-kappa B activation induced by TNF and $H_2O_2$, but not that activated by ceramide, lipopolysaccharides, or phorbol ester. *J. Immunol.* 168:2644-2651.
41. Dellabona, P., E. Padovan, G. Casorati, M. Brockhaus, and A. Lanzavecchia. 1994. An invariant V alpha 24-J alpha Q/V beta 11 T cell receptor is expressed in all individuals by clonally expanded CD4-8-T cells. *J. Exp. Med.* 180:1171-1176.
42. Brossay, L., M. Chioda, N. Burdin, Y. Koezuka, G. Casorati, P. Dellabona, and M. Kronenberg. 1998. CD1 d-mediated recognition of an alpha-galactosylceramide by natural killer T cells is highly conserved through mammalian evolution. *J. Exp. Med.* 188:1521-1528.
43. Exley, M. A., Q. He, O. Cheng, R. J. Wang, C. P. Cheney, S. P. Balk, and M. J. Koziel. 2002. Cutting edge: Compartmentalization of Th1-like noninvariant CD1d-reactive T cells in hepatitis C virus-infected liver. *J. Immunol.* 168:1519-1523.
44. Kita, H., O. V. Naidenko, M. Kronenberg, A. A. Ansari, P. Rogers, X. S. He, F. Koning, T. Mikayama, W. J. Van De, R. L. Coppel, M. Kaplan, and M. E. Gershwin. 2002. Quantitation and phenotypic analysis of natural killer T cells in primary biliary cirrhosis using a human CD1d tetramer. *Gastroenterology* 123:1031-1043.
45. Chen, J. F., Z. Huang, J. Ma, J. Zhu, R. Moratalla, D. Standaert, M. A. Moskowitz, J. S. Fink, and M. A. Schwarzschild. 1999. A(2A) adenosine receptor deficiency attenuates brain injury induced by transient focal ischemia in mice. *J. Neurosci.* 19:9192-9200.
46. Smart, Y. C., K. L. Stevenson, R. F. Thome, W. D. Thomas, L. H. Hsu, and R. C. Burton. 1989. Expression of natural killer (NK) cell-specific alloantigens on a mouse NK-like cell line. *Immunol. Cell Biol.* 67 (Pt 4):239-242.
47. Brossay, L., D. Jullien, S. Cardell, B. C. Sydora, N. Burdin, R. L. Modlin, and M. Kronenberg. 1997. Mouse CD1 is mainly expressed on hemopoietic-derived cells. *J. Immunol.* 159:1216-1224.

All cited publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for treating ischemia reperfusion injury (IRI), comprising: administering to a patient in need thereof a therapeutically effective amount of an agent that inhibits Natural Killer T (NKT) cells, wherein the agent is an anti-CD1 antibody or an anti-NK1.1 antibody.

2. The method of claim 1, wherein the agent inhibits NKT cells by depleting them.

3. The method of claim 1, wherein the agent inhibits NKT cells by interfering with them.

4. The method of claim 1, wherein the antibody is an anti-NK1.1 antibody.

5. The method of claim 4, wherein the anti-NK1.1 antibody is PK136.

6. The method of claim 1, wherein the anti-CD1 antibody is an anti-CD1a, anti-CD1b, anti-CD1c, or anti-CD1d antibody.

7. The method of claim 6, wherein the anti-CD1 antibody is selected from 10H3.9.3 (CD1a), BCD1b3 (CD1b), F10/21A3 (CD1c) and CD1d51 (CD 1d).

8. The method of claim 1, wherein the injury is selected from heart, kidney, skin, and liver ischemia-reperfusion injury.

9. The method of claim 1, wherein the IRI is liver IRI.

10. The method of claim 1, wherein the agent is administered orally, intravenously, intraperitoneally, or transdermally.

* * * * *